US006534083B2

(12) United States Patent
Gilding et al.

(10) Patent No.: US 6,534,083 B2
(45) Date of Patent: *Mar. 18, 2003

(54) HYDROGELS

(75) Inventors: Denis K. Gilding, Winsford (GB); Yimin Qin, Northwich (GB)

(73) Assignee: Advanced Medical Solutions Limited, Winsford (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/180,171

(22) PCT Filed: May 8, 1997

(86) PCT No.: PCT/GB97/01244

§ 371 (c)(1), (2), (4) Date: Jul. 26, 1999

(87) PCT Pub. No.: WO97/41900

PCT Pub. Date: Nov. 13, 1997

(65) Prior Publication Data

US 2002/0009591 A1 Jan. 24, 2002

(30) Foreign Application Priority Data

May 8, 1996 (GB) ............................................. 9609474

(51) Int. Cl.[7] ............................ A61F 13/00; A61L 15/00
(52) U.S. Cl. ........................................ 424/443; 424/449
(58) Field of Search .................................. 424/402, 443

(56) References Cited

U.S. PATENT DOCUMENTS

| 4,548,847 A | * 10/1985 | Aberson et al. |
| 4,956,350 A | * 9/1990 | Mosbey ........................ 514/55 |
| 5,210,117 A | * 5/1993 | Lee et al. ...................... 524/28 |
| 5,409,703 A | * 4/1995 | McAnallley et al. ......... 424/435 |
| 6,171,610 B1 | * 1/2001 | Vacanti et al. |
| 6,214,369 B1 | * 4/2001 | Grande et al. |

FOREIGN PATENT DOCUMENTS

| EP | 1 328 088 | * 8/1973 | ........... C08B/19/10 |
| EP | WO 89/12471 | * 6/1988 | ........... A61L/15/04 |
| EP | 0 227 955 | * 8/1995 | ........... A61F/13/00 |
| EP | 0 666 081 | * 8/1995 | ........... A61L/15/60 |

* cited by examiner

Primary Examiner—Thurman K. Page
Assistant Examiner—Isis Ghali
(74) Attorney, Agent, or Firm—Clifford W. Browning; Woodard, Emhardt, Naughton Moriarty & McNett

(57) ABSTRACT

A method of producing a hydrogel product comprises impregnating a coherent fibrous structure with an aqueous solution of a hydrogel precursor material said fibers incorporating cations which are capable of cross-linking said precursor material to form a fiber reinforced hydrogel as the hydrogel product.

10 Claims, No Drawings

HYDROGELS

The present invention relates to hydrogels, i.e. cross-linked macromolecular networks which are swollen with water or biological fluids. The invention relates more particularly, but not exclusively, to such hydrogels that are useful as wound dressings.

A hydrogel is a cross-linked macromolecular network swollen with water or biological fluids. It is known that hydrogels are useful as wound dressings, particularly because of their ability to donate fluid to a wound to maintain a moist "healing environment". There are however disadvantages with prior art hydrogel dressings (e.g. Clearsite) in that they can be weak and difficult to handle.

It is therefore an object of the present invention to obviate or mitigate the above disadvantages.

According to a first aspect of the present invention there is provided a method of producing a hydrogel product comprising impregnating a coherent fibrous structure (preferably sterilised) with an aqueous solution of a hydrogel precursor material (preferably sterilised), said fibers incorporating cations which are capable of cross-linking said precursor material to form a fiber reinforced hydrogel as the hydrogel product.

By "coherent fibrous structure" we mean that the fibrous structure is comprised of fibres which are positively held together to maintain the overall coherency of the structure although obviously we do not preclude the possibility that individual fibres of the structure may become loose and detached. Such structures are to be distinguished from, for example, loose chopped fibres in which there is no mechanical forces holding the fibres together into the form of a structure. Examples of coherent fibrous structures which may be used in accordance with the invention are knitted, woven, and non-woven products such as felts, matts and the like. A preferred fibrous structure is a non-woven felt.

A particularly preferred fibrous structure is a non-woven felt made of calcium alginate fibres and having a basis weight of 30 to 200 gsm, more preferably 40 to 80 gsm, and most preferably about 60 gsm.

The method of the invention is effected by impregnating the fibrous structure with the solution of hydrogel precursor, preferably in ratio (by weight) of solution:fabric of (20–70):1. The method results in the production of a hydrogel which has been cross-linked (i.e. "set") by ions released from the fibres. In the final hydrogel the fibrous structure provides, in effect, a reinforcement giving strength for easy handling of the hydrogel. If desired the hydrogel product may be autoclaved.

Hydrogels produced in accordance with the invention may be in the form of sheets typically having a thickness of 1 mm to 10 mm.

The hydrogels are in a hydrated form and are capable of donating moisture to a wound. The hydrogels may be used for treating superficial wounds with low to medium levels of exudates Examples of hydrogel precursor material which may be used include sodium alginate, sodium carboxymethyl cellulose, sodium pectinate, sodium O-carboxymethyl chitosan (OCC), sodium N,O-carboxymethyl chitosan (NOCC), sodium polyacrylate, and naturally occurring gums and synthetic polymers containing pendant carboxylic acid groups (hummectants).

The hydrogel precursor may consist wholly or partially of Ace Mannan (or other component of Alloe Vera) which is a natural polymer known to accelerate healing of wounds. The Ace Mannan may, for example, provide up to 80% of the matrix. The Ace Mannan may be clinical grade material obtainable from Carrington Laboratories, Dallas, Tex., U.S.A.

The hydrogel precursor may, if desired, incorporate an agent to stimulate the healing of wounds. Examples of such agents include growth factors, e.g. whey growth factor extract (obtainable from GroPep Ltd. Australia) or Prezatide copper acetate complex (obtainable from Procyte, U.S.A.), The fibres which are used contain a di- or higher valent cation which is effective for cross-linking the hydrogel. Examples of suitable cations include $Ca^{2+}$, $Zn^{2+}$, and cations which also act as enzyme cofactors. Particular preferred examples of fibres which may be used are calcium alginate fibres.

Preferably the hydrogel precursor solution incorporates a bacteriostatic agent, preferably propylene glycol.

In a preferred method of carrying out the invention, the hydrogel precursor (e.g. an alginate) is dissolved in a mixture of 75%-85% by weight water and 15% to 25% by weight propylene glycol. The resultant solution is then used to impregnate the coherent fibrous structure to form the hydrogel.

It is possible for the hydrogel precursor solution and coherent fibrous structure to be supplied separately whereby the method of the first aspect of the invention may be effected in, for example, a surgery. This affords the possibility of either using the coherent fibrous structure as a dressing per se or using it to produce a hydrogel product as discussed above.

Therefore according to a second aspect of the invention there is provided a kit of parts for producing a hydrogel product the kit comprising a container of a hydrogel precursor solution (preferably sterilised) and a coherent fibrous structure (preferably sterilised).

Hydrogel products obtained in accordance with the invention may be used in conjunction with hydrophilic films which have an increased breathability in the presence of liquid water as compared to moisture vapour alone. The use of such a film over the hydrogel (i.e. on the side remote from the wound) ensures that water is vented from the hydrogel through the film. Therefore the dissolution of the hydrogel may be controlled, Typically the breathable film will be of a material which, as a 50 micron film, has an MVTR in the presence of moisture vapour alone of 6,000 to 10,000 g $m^{-2}$ 24 $hr^{-1}$ as measured by ASTM E96B and an MVTR in the presence of a liquid water (as measured by ASTM E96BW) of 6,000 to 10,000 g $m^{-2}$ 24 $hr^{-1}$. Typically the breathable film will lave a thickness of 30–70 microns, more preferably 40–60 microns, e.g. about 50 microns.

The breathable film may for example be of polyurethane. Suitable films are available from Innovative Technologies Limited under the designations IT325, IT425 and IT625.

The invention is illustrated with reference to the following non-limiting Example.

EXAMPLE

A none-woven felt made of calcium alginate MF1-2A felt, available from Innovative Technologies) having a weight/unit area of about 60 g/m² was treated with a 2% alginate (Protanol LF 10/60, ex-Pronava) dissolved in a 80/20 mixture of water and propylene glycol. The ratio of solution to felt was 40 to 1. The solution was first spread out in a flat stainless steel dish having a size of about 30 cm×30 cm and the felt was then placed in solution. The fibres interacted with the sodium alginate in the solution to form a sheet hydrogel. The resultant gel could be autoclaved to provide a hydrated sheet hydrogel for treating superficial wounds with low to medium level of exudate.

What is claimed is:

1. A method of producing a hydrogel sheet having fibre reinforcement, comprising the steps of impregnating a coherent calcium alginate fibrous structure with an aqueous solution of a sodium alginate hydrogel precursor material that are cross-linked to form a hydrogel, the fibres of the fibrous structure incorporating calcium ion cations which are donated to cross-link said hydrogel precursor material, and effecting formation of a hydrogel by cross-linking of the hydrogel precursor material by calcium ion cations donated from said fibres so as to form a fibre reinforced hydrogel sheet.

2. A method as claimed in claim 1 wherein the coherent fibre structure is knitted, woven or non-woven.

3. A method as claimed in claim 2 wherein the coherent fibre structure is a felt or matt.

4. A method as claimed in claim 1 wherein the hydrogel precursor is selected from the group consisting of sodium alginate, sodium carboxymethyl cellulose, sodium pectinate, sodium O-carboxymethyl chitosan, sodium N,O-carboxymethyl chitosan, sodium polyacrylate, naturally occurring gums and synthetic polymers containing pendant carboxylic acid groups.

5. A method as claimed in claim 1 wherein the hydrogel precursor consists wholly or partially of a component of Alloe Vera.

6. A method as claimed in claim 1 wherein the hydrogel precursor incorporates a healing agent that stimulates the healing of wounds.

7. A method as claimed in claim 1 wherein the hydrogel precursor is dissolved in a mixture of 75% to 85% by weight water and 15% to 25% by weight propylene glycol.

8. A method as claimed in claim 1 wherein the ratio by volume of the hydrogel precursor solution to the coherent fibre structure is 20 to 70:1.

9. A method of producing a hydrogel sheet having fibre reinforcement, comprising the steps of impregnating a coherent fibrous structure with an aqueous solution of a hydrogel precursor material that are cross-linked to form a hydrogel, the fibres of the fibrous structure incorporating calcium ion cations which are donated to cross-link said hydrogel precursor material, and effecting formation of a hydrogel by cross-linking of the hydrogel precursor material by calcium ion cations donated from said fibres so as to form a fibre reinforced hydrogel sheet.

10. A method as claimed in claim 5 wherein the hydrogel precursor consists wholly or partially of Ace Mannan.

* * * * *